United States Patent [19]
Firoozabady et al.

[11] Patent Number: 5,792,927
[45] Date of Patent: Aug. 11, 1998

[54] GENETICALLY TRANSFORMED ROSE PLANTS AND METHODS FOR THEIR PRODUCTION

[75] Inventors: Ebrahim Firoozabady, Pleasant Hill; Karol Robinson, Moraga, both of Calif.

[73] Assignee: Florigene Europe B.V., Victoria, Australia

[21] Appl. No.: 461,331

[22] Filed: Jun. 5, 1995

Related U.S. Application Data

[62] Division of Ser. No. 154,143, Nov. 18, 1993, Pat. No. 5,480,789, which is a continuation of Ser. No. 678,846, Apr. 1, 1991, abandoned.

[51] Int. Cl.$^6$ .............................. A01H 5/00; C12N 15/82; C12N 15/00; C12N 1/20
[52] U.S. Cl. .................. 800/205; 435/172.3; 435/252.2; 435/419; 435/430.1; 800/DIG. 36
[58] Field of Search .......................... 435/172.3, 240.45, 435/240.48, 240.49, 252.2, 419, 430.1; 800/205, DIG. 36

[56] References Cited

U.S. PATENT DOCUMENTS 4,672,035  6/1987  Davidonis et al. ............... 435/427

FOREIGN PATENT DOCUMENTS 1241334  8/1960  France .
1423068  1/1966  France .

OTHER PUBLICATIONS

Ammirato, et al. (eds.); *Handbook of Plant Cell Culture*; Chapter 29, pp. 716–743; 1990.
An; *Plant Physiol.*; Issue 79, pp. 568–570; 1985.
Bolton, G.W., et al.; *Science*; vol. 232, pp. 983–985; 1986.
Brown, Daniel C.W.; *Cell Structure and Somatic Cell Genetics of Plants*; vol. 3, chap. 2, pp. 49–50; 1986.
Burger, D.W.; *Plant Cell Tissue and Organ Culture*; vol. 21, pp. 147–152; 1990.
Chabaud, et al.; *Plant Cell Reports*; vol. 7, pp. 512–516; 1988.
Constabel, F., et al.; *Cell Culture and Somatic Cell Genetics of Plants*; vol. 1, pp. 27–35; 1984.
Deak, et al.; *Plant Cell Reports*; vol. 5, pp. 97–100; 1986.
de Cleene, et al.; *The Botanical Review*; vol. 42, pp. 389–466; 1976.
de Cleene, et al.; *The Botanical Review*; vol. 47, pp. 147–194; 1981.
de Wit, J., et al.; *Plant Cell Reports*; vol. 9, pp. 456–458; 1990.
Firoozabady, et al.; *Bio/Technology*; vol. 12, pp. 609–613; Jun. 1994.
Gordon-Kamm, et al.; *Plant Cell*; vol. 2, pp. 603–618; 1990.
Graham, et al.; *Plant Cell Tissue and Organ Culture*; vol. 20, pp. 35–39; 1990.
Hasegawa, P.; *Hort Science*; vol. 14, pp. 610–612; 1979.
Ishioka, et al.; *Plant Cell Tissue and Organ Culture*; vol. 22, pp. 197–199; 1990.
James, et al.; *Plant Cell Reports*; vol. 7, pp. 658–661; 1989.
Khatamian, H., et al.; *VIIIth International Congress on Plant Tissues and Cell Culture*; p. 256 *abstract B4–63*; 1990.
Khosh-Khui, et al.; *J. Hort Science*; vol. 57, pp. 315–319; 1982.
Lloyd, et al.; *Euphytica*; vol. 37, pp. 31–36; 1988.
Matthews, D., et al.; *VIIth Congress on Plant Tissue and Cell Culture*; p. 69, *abstract A2–99*; 1990.
McHughen, et al.; *J. Plant Physiol.*; vol. 135, pp. 245–248; 1989.
Michelmore, et al.; *Plant Cell Reports*; vol. 6, pp. 439–442; 1987.
Muller, et al.; *Biochemical Biophys. Res. Comm.*; vol. 123, pp. 458–462; 1984.
Noriega, et al.; *Abstract A203*; Jun. 24–29, 1990.
Radke, et al.; *Theo. Appl. Genet.*; vol. 75, pp. 685–694; 1988.
Roberts, A.V., et al.; *Symposium Proceedings: Integration of in vitro Techniques in Ornamental Plant Breeding, Wageningen, Netherlands*; pp. 110–115; Nov. 10–14, 1990.
Rout, G.R., et al.; *Plant Cell Tissue and Organ Culture*; vol. 27, pp. 65–69; 1991.
Rout, G.R., et al.; *Abs. Orissa J. of Hort.*; vol. 17(1–2), pp. 46–49; 1989.
Scorza; *In Vitro Cell Devel. Biol.*; vol. 26, pp. 829–834; 1990.
Skirvin, et al.; *Hort Science*; vol. 14, pp. 608–610; 1979.
Valles; *Acta Horticulturae*; vol. 212, pp. 691–696; 1987.
Valvekans, et al.; *PNAS USA*; vol. 85, 5536–5540; 1988.
van der Mark, F., et al.; *J. Genet. & Breed*; vol. 44, pp. 263–268; 1990.
Wang, Dayuan, et al.; *Hort Science*; vol. 19(1), pp. 71–72; 1984.
Zimmerman, R.H.; *Cell Culture and Somatic Cell Genetics of Plants*; vol. 3, chap. 12, pp. 243–252; 1986.

Primary Examiner—Douglas W. Robinson
Assistant Examiner—Thanda Wai
Attorney, Agent, or Firm—Townsend and Townsend and Crew LLP

[57] ABSTRACT

Rose plant cells are transformed by incubation with Agrobacterium cells carrying an exogenous DNA sequence. The callus cells may be obtained from various tissue sources, including stamen filaments, leaf explants, and the like, and whole rose plants may be regenerated from the transformed callus cells. The exogenous DNA will be stably incorporated into the chromosomes of the regenerated rose plant which will be able to express gene(s) encoded by the DNA sequence.

15 Claims, 2 Drawing Sheets

GENETICALLY TRANSFORMED ROSE PLANTS AND METHODS FOR THEIR PRODUCTION

This application is a division of application Ser. No. 08/154,143, filed on Nov. 18, 1993, now U.S. Pat. No. 5,480,789; which in turn is a continuation of application Ser. No. 07/678,846, filed Apr. 1, 1991, now abandoned.

The subject matter of the present invention is related to that of application Ser. No. 07/542,841, filed Jun. 25, 1990, the full disclosure of which is incorporated herein by reference.

BACKGROUND OF THE INVENTION

1. Field of the Invention

The present invention relates generally to methods for genetically altering the cells of higher plants. More particularly, the invention relates to a method for genetically transforming cells from rose plants.

The hybrid tea rose, *Rosa hybrida*, is one of the most popular of all cultivated plants. As with any valuable plant species, breeders have long been working to improve existing varieties and create new varieties using conventional cross-breeding techniques. Characteristics of particular interest include color, fragrance, morphology, herbicide resistance, pesticide resistance, environmental tolerance, vase life of the cut flower, and the like. While improvements and variations in most or all of these areas have been achieved, progress is slow because of the perennial nature of the plant and the high incidence of plant sterility caused by abnormal chromosome numbers. While rose tissue culture is now possible based on work described in co-pending application Ser. No. 542,841, referenced above, the natural genetic variation offered by tissue culture is random and still requires substantial effort to produce a particular genetic variation.

For these reasons, it would be desirable to use recombinant DNA technology to produce new rose cultivars in a controlled and predictable manner. It would be particularly desirable to be able to genetically transform individual rose plant cells to introduce a desired characteristic and to be able to regenerate viable somatic embryos and rose plantlets from the modified cells. Such methods should be capable of introducing preselected exogenous genes to the rose plant cell and should permit selection of transformed cells which are capable of expressing the gene. The method should produce regenerated rose plants which have stably incorporated the gene(s).

2. Description of the Background Art

Abstract A203 (Noriega et al.) in *Abstracts VIIth International Congress on Plant Tissue and Cell Culture*, Amsterdam, Jun. 24–29, 1990, reports preliminary results on the production of calli from rose (*Rosa hybrida*) leaves. The reported results correspond to work described in related application U.S. Ser. No. 542,841, previously incorporated herein by reference.

Tissue culture methods involving *Rosa hybrida* and other rose species are described in Handbook of Plant Cell Culture, Ammirato et al. (eds.), Chapter 29, 716–743, McGraw-Hill (1990); Skirvin et al. (1979) Hort Sci., 14:608–610; Hasegawa (1979) Hort Sci., 14:610–612; KhoshKhui et al. (1982) J. Hort Sci., 57:315–319; Valles (1987) Acta Horticulturae, 212:691–696; Lloyd et al. (1988) Euphytica, 37:31–36; Burger (1990;) Plant Cell Tissue and Organ Culture, 21:147–152; Ishioka et al. (1990) Plant Cell, Tissue and Organ Culture, 22:197–199; Matthews et al. "A Protoplast to Plant System in Roses", 7th IAPTC Congress, Amsterdam; and de Wit et al. (1990) Plant Cell Reports, 9:456–458.

The susceptibility of certain Rosa species to infection and tumor induction by Agrobacterium tumefaciens is described in De Cleene et al. (1976) The Botanical Review, 42:389–466. The susceptibility of certain Rosa species to infection and hairy root induction by *Agrobacterium rhizogenes* is described in De Cleene et al. (1981) The Botanical Review, 47:147–194.

The transformation of embryogenic calli from *Prunus persica* (a member of the Rosaceae family) with *Agrobacterium tumefaciens* is reported in Scorza (1990) In Vitro Cell Dev. Biol., 26:829–834. No disclosure of transformed plant material beyond callus stage or of regeneration of whole plants is provided. The transformation of explant materials from other members of the Rosaceae family is described in James et al. (1989) Plant Cell Reports, 7:658–661, and Graham et al. (1990) Plant Cell, Tissue and Organ Culture, 20:35–39.

The transformation of crushed tobacco callus with wild type (virulent) *Agrobacterium tumefaciens* resulting in crown gall formation is reported in Müller et al. (1984) Biochem. and Biophys. Res. Comm., 123:458–462.

SUMMARY OF THE INVENTION

The present invention comprises methods for genetically transforming rose plant callus cells and, in the preferred embodiments, for regenerating the transformed callus cells into somatic embryos and ultimately back into viable rose plantlets. The callus cells are transformed by incubation with Agrobacterium cells carrying an exogenous DNA sequence which typically includes a selectable marker gene as well as one or more genes to be expressed. Transformed callus cells are selected, typically on a medium which inhibits growth in the absence of the marker, and may be regenerated into somatic embryos and plantlets which stably incorporate the DNA sequence(s).

The present invention further comprises rose callus cells, somatic rose embryos, and rose plantlets which incorporate exogenous DNA sequences. Preferably, such transformed cells, embryos, and plantlets are obtained by the methods of the present invention.

The methods of the present invention provide a particularly convenient technique for selectively breeding new rose cultivars in a predictable and expeditious manner. It is expected that a variety of traits, such as color, fragrance, morphology, herbicide resistance, pesticide resistance, flower vase life, environmental tolerance, other horticultural traits, and may be intentionally introduced into the callus cells and stably incorporated into the chromosomes of the regenerated embryos and plantlets.

DESCRIPTION OF THE SPECIFIC EMBODIMENTS

Figure 1:
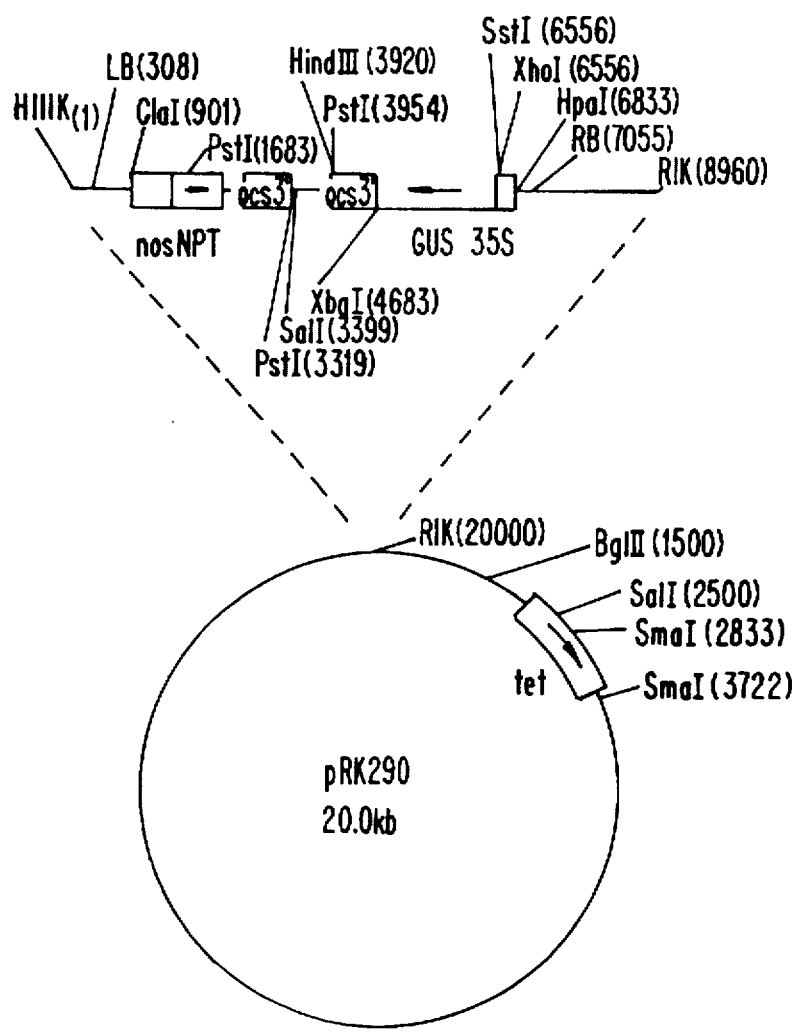
FIG. 1 is a map of binary plasmid pJJ3499 used in Example 1 in the Experimental section hereinafter.

According to the present invention, genetically transformed rose plants, cells, and embryos are obtained by the selective introduction of exogenous DNA sequence(s) into the chromosomes of cultured rose callus cells. The methods require certain starting materials, including a source of rose plant material to produce callus cells, the DNA sequence(s) to be introduced, Agrobacterium cells to carry the DNA sequence(s) and mediate their transfer to the rose callus cells, and culture media suitable for the steps of callus induction, DNA transfer, and embryo and plantlet regeneration, as described in much greater detail hereinbelow. Each of the necessary starting materials will now be described.

The following terms, as used in the specification and claims, are intended to have the following meanings.
Somatic embryo: Structures similar to zygotic embryos which arise from somatic cells.
Embryonic: Capable of becoming somatic embryos.
In rose calli have surface structures (e.g., about 0.5 mm to 1 mm) which are capable of becoming embryos.
Pre-embryogenic: Capable of becoming embryogenic. In rose, these calli are friable, whitish-creamish, granular.
Callus: Undifferentiated cell mass produced usually by culture of different organs in vitro. It can be hard, soft, dispersible, compact, spongy, dry, watery, or etc.
Callus Structures: See above.
Somatic Cell: Any of the body of an organism except the germ cells (sexual reproductive cells).

Rose plant tissue which is used for producing callus cells may be obtained from any species of the rose genus, Rosa. Exemplary species include *Rosa damascena*, *Rosa multiflora*, *Rosa gallica*, *Rosa hybrida*, and the like. Of particular interest are various cultivars of *Rosa hybrida*, such as Royalty, Frisco, Sonia, and the like.

The plant tissue used for the production of callus cells may be mature or immature, preferably being mature somatic tissue. Suitable immature plant tissue can be obtained from in vitro plant tissue culture techniques, such as those described in Ammirato et al. (eds), *Handbook of Plant Cell Culture*, vol. 5, McGraw-Hill Publishing Co., New York, 1990, particularly at Chapter 29, pages 716–747, the disclosure of which is incorporated herein by reference. Callus cells obtained from tissue culture materials may be subjected to a "cell suspension" step prior to transformation as described below. Such cell suspension comprises suspending the cells in a liquid culture medium and shaking the suspension, typically at about 100 to 500 rpm. In some cases, cell suspension may be useful to the production of embryonic cells.

The preferred mature somatic plant tissues may be obtained from any part of the mature rose plant that is capable of producing calli. Suitable plant parts include stamen filaments, leaf explants, stem sections, shoot tips, petal, sepal, petiole, peduncle, and the like, with stamen filaments and leaf explants being particularly preferred.

Generally, the mature plant tissue sources will be disinfected prior to introduction to the callus induction culture. A suitable disinfection step comprises an alcohol wash, e.g., with 75% ethanol for about one minute, followed by a wash with bleach (10%) and a suitable detergent, e.g., 0.1% Tween®, for 20 minutes. The plant materials are then rinsed, usually two to three times for about five minutes each time, with sterile, deionized water prior to culturing.

Suitable stamen filaments will have a length from about 0.5 to 1.5 cm, preferably being about 1 cm. The stem and leaf sections are preferably cut to a size below about 1 cm×1 cm, preferably being about 0.5 cm×0.5 cm. Shoot tips will be cut to a length in the range from about 0.5 to 3 mm, preferably being about 1 mm in length.

The exogenous DNA sequences to be introduced will usually carry at least one selectable marker gene to permit screening and selection of transformed callus cells (i.e., those cells which have incorporated the exogenous DNA into their chromosomes), as well as one or more "functional" genes which are chosen to provide, enhance, suppress, or otherwise modify expression of a desired trait or phenotype in the resulting plant. Such traits include color, fragrance, herbicide resistance, pesticide resistance, disease resistance, environmental tolerance, morphology, growth characteristics, and the like.

The functional gene to be introduced may be a structural gene which encodes a polypeptide which imparts the desired phenotype. Alternatively, the functional gene may be a regulatory gene which might play a role in transcriptional and/or translational control to suppress, enhance, or otherwise modify the transcription and/or expression of an endogenous gene within the rose plant. It will be appreciated that control of gene expression can have a direct impact on the observable plant characteristics. Other functional "genes" include sense and anti-sense DNA sequences which may be prepared to suppress or otherwise modify the expression of endogenous genes. The use of anti-sense is described generally in van der Krol et al., (1990) Mol. Gen. Genet. 220:204–212, the disclosure of which is incorporated herein by reference. The use of sense DNA sequences is described in various references, including Napoli et al. (1990) Plant Cell, 2:279–289 and van der Krol et al. (1990) Plant Cell, 2:291–299, the disclosures of which are incorporated herein by reference.

Structural and regulatory genes to be inserted may be obtained from depositories, such as the American Type Culture Collection, Rockville, Md. 20852, as well as by isolation from other organisms, typically by the screening of genomic or cDNA libraries using conventional hybridization techniques, such as those described in Maniatis et al., *Molecular Cloning—A Laboratory Manual*, Cold Spring Harbor Laboratory, Cold Spring Harbor, N.Y. (1985). Screening may be performed by (1) nucleic acid hybridization using homologous genes from other organisms, (2) probes synthetically produced to hybridize to particular sequences coding for desired protein sequences, or (3) DNA sequencing and comparison to known sequences. Sequences for specific genes may be found in various computer databases, including GenBank, National Institutes of Health, as well as the database maintained by the United States Patent Office.

The genes of interest may also be identified by antibody screening of expression libraries with antibodies made against homologous proteins to identify genes encoding for homologous functions. Transposon tagging can also be used to aid the isolation of a desired gene. Transposon tagging typically involves mutation of the target gene. A mutant gene is isolated in which a transposon has inserted into the target gene and altered the resulting phenotype. Using a probe for the transposon, the mutated gene can be isolated. Then, using the DNA adjacent to the transposon in the isolated, mutated gene as a probe, the normal wild-type allele of the target gene can be isolated. Such techniques are taught, for example, in McLaughlin and Walbot (1987) Genetics, 117:771–776; Dooner et al. (1985) Mol. Gen. Genetics, 200:240–246; and Federoff et al. (1984) Proc. Natl. Acad. Sci. USA, 81:3825–3829, the disclosures of which are incorporated herein by reference.

Particular genes which may be incorporated into rose callus cells according to the method of the present invention include the chalcone synthase gene (Napoli et al. (1990) Plant Cell 2 279:289) and the insect resistance gene (Vaeck et al. (1987) Nature 328:33).

The selectable marker gene on the DNA sequences to be inserted will usually encode a function which permits the survival of transformed callus cells in a selective medium. Usually, the selectable marker gene will encode antibiotic resistance, particularly kanamycin resistance, hygromycin resistance, streptomycin resistance, chlorosulfuron resistance, (herbicide resistance), or the like. The composition of a suitable selective medium is described hereinbelow.

In addition to the "functional" gene and the selectable marker gene, the DNA sequences may also contain a reporter gene which facilitates screening of the transformed callus cells and plant material for the presence and expression of the exogenous DNA sequences. Exemplary reporter genes include β-glucuronidase and luciferase, as described in more detail hereinafter.

The exogenous DNA sequences will be introduced to the callus cells by incubation with Agrobacterium cells which carry the sequences to be transferred within a transfer DNA (T-DNA) region found on a suitable plasmid, typically the Ti plasmid. Ti plasmids contain two regions essential for the transformation of plant cells. One of these, the T-DNA region, is transferred to the plant nuclei and induces tumor formation. The other, referred to as the virulence (vir) region, is essential for the transfer of the T-DNA but is not itself transferred. By inserting the DNA sequence to be transferred into the T-DNA region, introduction of the DNA sequences to the plant genome can be effected. Usually, the Ti plasmid will be modified to delete or inactivate the tumor-causing genes so that they are suitable for use as vector for the transfer of the gene constructs of the present invention. Other plasmids may be utilized in conjunction with Agrobacterium for transferring the DNA sequences of the present invention to callus cells.

The construction of recombinant Ti plasmids may be accomplished using conventional recombinant DNA techniques, such as those described in Maniatis et al., supra. Frequently, the plasmids will include additional selective marker genes which permit manipulation and construction of the plasmid in suitable hosts, typically bacterial hosts other than Agrobacterium, such as E. coli. Suitable selective marker genes include tetracycline resistance, kanamycin resistance, ampillcilin resistance, and the like.

The genes within the DNA sequences will typically be linked to appropriate transcriptional and translational control sequences which are suitable for the rose plant host. For example, the gene will typically be situated at a distance from a promoter corresponding to the distance at which the promoter is normally effective in order to ensure transcriptional activity. Usually, a polyadenylation site and transcription termination sites will be provided at the 3'-end of the gene coding sequence. Frequently, the necessary control functions can be obtained together with the structural gene when it is isolated from a target plant of other host. Such intact genes will usually include coding sequences, intron(s), a promoter, enhancers, and all other regulatory elements either upstream (5') or downstream (3') of the coding sequences.

Optionally, a binary vector system may be used to introduce the DNA sequences according to the present invention. A first plasmid vector strain would carry the T-DNA sequence while a second plasmid vector would carry a virulence (vir) region. By incubating Agrobacterium cells carrying both plasmids with the callus cells, infection of the callus cells can be achieved. See, Hoekema et al. (1983) Nature 303:179–180, the disclosure of which is incorporated herein by reference.

Suitable Agrobacterium strains include *Agrobacterium tumefaciens* and *Agrobacterium rhizogenes*. While the wild-type *Agrobacterium rhizogenes* may be used, the *Agrobacterium tumefaciens* should be "disarmed," i.e., have its tumor-inducing activity removed, prior to use. Preferred *Agrobacterium tumefaciens* strains include LBA4404, as described by Hoekema et al. (1983) Nature, 303:179–180, and EHA101 (Hood et al. (1986) J. Bacteriol., 168:1291–1301. A preferred *Agrobacterium rhizogenes* strain is 15834, as described by Birot et al. (1987) Plant Physiol. Biochem., 25:323–325.

After the Agrobacterium strain(s) carrying the desired exogenous DNA sequence(s) have been prepared, they will usually be cultured for a period of time prior to incubation with the rose callus cells. Initially, the Agrobacterium may be cultured on a solid media including nutrients, an energy source, and a gelling agent. Suitable nutrients include salts, tryptone, and yeast extracts, while most sugars are suitable as the energy source and the gelling agent can be agar, Gel-rite®, or the like. A preferred medium is L-Broth, which is described in detail in the Experimental section hereinafter. Usually, medium will include an antibiotic to select for Agrobacterium carrying the plasmid DNA sequences.

The Agrobacterium cells are typically cultured for about one to three days, preferably in the dark at about 28° C., and are collected while still a white-creamish color, i.e., before browning, typically by being scraped off the solid medium. The cells are then suspended in a liquid medium, e.g., L-broth, or more preferably in an induction broth containing the following components:

| | Broad Range | Preferred |
| --- | --- | --- |
| Ammonium chloride | 0.5–3 g/l | 1 g/l |
| Magnesium sulfate | 0.5–3 g/l | 1 g/l |
| Potassium chloride | 0.05–2 g/l | 0.15 g/l |
| Calcium | 2–20 mg/l | 10 mg/l |
| Ferrous sulfate | 0.5–10 mg/l | 2.5 mg/l |
| Phosphate monobasic | 50–1000 mg/l | 272 mg/l |
| MES | 1000–10,000 mg/l | 3904 mg/l |
| Glucose | 2–30 g/l | 5 g/l |
| Acetosyringone | 10–200 μM | 100 μM |
| Sucrose | 10–30 g/l | 20 g/l |
| pH | 5–7 | 5.5 |

The Agrobacterium cells are cultured in the L-broth or induction broth for about one to ten hours, preferably from about two to three hours, while being agitated, preferably at moderate temperatures from about 20° C. to 30° C.

Rose callus cells which may be transformed according to the method of the present invention may be produced as described in copending application Ser. No. 542,841, the disclosure of which has previously been incorporated herein by reference. Rose tissue is obtained from any of the plant parts described above and placed in a callus induction medium including suitable nutrients, an energy source, growth regulators, and the like, selected to induce callus formation in the plant material. A variety of basal nutrient media are known which provide adequate supplies of nitrogen and salts to support callus growth, such as White's, B5, N6 and MS medium. Any sugar may be employed as energy source. Among the appropriate choices are glucose, maltose, sucrose, or lactose, or sucrose in combination with any of the named sugars, or mannose. A preferred sugar for this purpose is sucrose, at a level of about 10–50 g/l, but molar equivalents of other sugars may also be employed.

Callus induction medium preferably contains at least one auxin and at least one cytokinin. The auxins may be any auxin, natural or synthetic, for example, indole acetic acid (IAA), naphthalene acetic acid (NAA), 2,4dichlorophenoxy acetic acid (2,4-D), picloram, and dicamba. The cytokinin may be selected from any of the known cytokinins, natural or synthetic, for example 6-benzyladenine (6-BA), zeatin (ZEA), kinetin (KIN), and isopentyladenosine (iP). Callus may be induced in the presence of several combinations of auxin and cytokinin. However, superior results are observed on an induction medium comprising 2,4-D and zeatin. An alternate useful combination is NAA with kinetin. Generally, an auxin will be present in an amount of about 0.1 to 10 mg/ml, and cytokinin in an amount of about 0.2 to 15.0 mg/ml. When the auxin is NAA, the concentration in the medium is preferably from about 0.5 to 2.5 mg/ml, and most preferably about 2.0 mg/ml. When 2,4-D is used, the amount is preferably from about 0.5 to 10.0 mg/ml and most preferably about 2.5 mg/ml. When the cytokinin is kinetin, the concentration in the medium is preferably from about 0.5 to 5 mg/ml and most preferably about 0.5 mg/ml. When zeatin is used, the concentration is preferably from about 0.2 to 12.5 mg/ml and most preferably about 1.5 mg/ml. Other nonessential components may also be added to the medium to optimize callus induction. For example, amino acids, such as glycine, may be employed as a nitrogen source. In certain embodiments, use of additional growth regulators may be helpful in promoting callus induction. For example, addition of abscisic acid (ABA), in the amount of about 0.1 to 0.2 mg/l may be useful in callus induction, particularly to promote a more globular callus, which leads to embryogenic tissue. ABA may be used with all explant sources, but has been especially useful with the culture of in vitro leaf explants.

Those skilled in the art will recognize that other components which are frequently employed in plant tissue culture may also be incorporated in the callus induction medium. Addition of various vitamins, e.g., MS vitamins, White vitamins, nicotinic acid, inositol, pyridoxine or thiamine is common. Similarly, for solid media, an appropriate amount of solidifying agent, such as agar or Gel-rite®, is also added to the mixture.

The rose tissue is cultured on the callus induction medium for a time sufficient to produce at least one callus which serves as a source of dispersed callus cells for transformation according to the present invention. Typically, tissue may be maintained in the callus induction medium for from about three to thirteen weeks, usually from about seven to ten weeks, and preferably for about eight weeks, to yield a fast growing callus. Initially, callus morphology may be hard, spongy, watery, sandy, or globular, and may have a white, cream, or yellow color, depending on the particular composition of the medium. The preferred morphology for use in the transformation methods of the present invention occurs after from about seven to ten weeks, usually at about eight weeks, when the calli become highly friable or dispersable with a whitish-creamish color and a granular consistency.

While cells from calli having these characteristics have been found to be most suitable, cells from calli which are hard and compact may also be used for transformation by cutting into small sections, typically having dimensions of about 2 to 3 mm.

Calli cultured as just described may be used directly as the source of callus cells for transformation or may be subcultured prior to use as a starting material. Subculturing allows the continuing maintenance of callus cells as a source of starting materials for the method of the present invention.

In order to achieve the desired transformation, the callus material described above is incubated with the Agrobacterium cells carrying the exogenous DNA sequence to be transferred, typically for about one to four days. Incubation is achieved in a cocultivation medium which includes nutrients, an energy source, and an induction compound which is selected to induce the virulence (vir) region of Agrobacterium to enhance transformation efficiency. The induction compound can be any phenolic compound which is known to induce such virulence, preferably being acetosyringone (AS) present at from about 10 to 200 µM, preferably at about 100 µM. Suitable phenolic compounds are described in Bolton et al. (1986) Science 232:983–985.

The preferred cocultivation medium includes sucrose (20 g/l) as the energy source, 2,4-D (5 mg/l) as the auxin, and zeatin (1 mg/l) as the cytokinin. Gibberellic acid (1 mg/l) is also preferably present as a growth regulator. A preferred formulation for the cocultivation medium is N12AS set forth in the Experimental section hereinafter.

Callus cells are combined with the Agrobacterium cells in the cocultivation medium at a moderate temperature, typically in the range from about 20° to 28° C., preferably at about 24° C., from about one to four days, usually from about one to two days. The medium is preferably kept in the dark, and the cocultivation continued until the Agrobacterium have grown sufficiently so that colonies are observable on the calli, either directly or through a microscope.

The Agrobacterium cells are present at a concentration from about $10^7$ to $10^{10}$ cells/ml, preferably at about $10^9$ cells/ml. The callus cells are present at a ratio of from about 1:1 to about 10:1 (callus cells:Agrobacterium cells), preferably at about 3:1, on a volume basis. Usually, a total of about 1 to 100 ml of callus material is used, preferably about 10 ml, in a total culture volume of about 1 to 100 ml, preferably about 10 to 12 ml. Preferably, the callus cells and Agrobacterium cells are placed on a filter paper matrix, such as Whatman #1, on the cocultivation medium.

After transformation is completed, the callus cells are washed from the Agrobacterium cells with water or a culture medium containing nutrients, an energy source, growth regulators, and the like. For smaller callus structures, typically in the range from about 0.2 to 0.3 mm in size, use of N12 medium (see the Experimental section hereinafter) is particularly suitable. For larger callus structures, typically from about 0.4 to 0.7 mm in size, use of M53 medium is particularly suitable.

The transformed calli are mixed with the wash medium, typically at a volume ratio of from about 1:3 to about 1:30 (calli:liquid), preferably at about 1:10, and centrifuged, preferably at 500 rpm for about 5 minutes. The resulting liquid fraction containing most of the bacteria is removed, while the denser fraction containing the calli is saved. The wash is repeated, typically from two to six times, with antibiotics being used in at least the later washes in order to kill any remaining Agrobacterium cells. Any antibiotic capable of killing Agrobacterium may be used, with carbenicillin (200 to 1000 mg/l), vancomycin (100 to 500 mg/l), cloxacillin (200 to 1000 mg/l) cefotaxin (200 to 1000 mg/l), and erythromycin (200 to 1000 mg/l), being preferred.

After washing, the calli are placed on a suitable selection medium including a plant selection agent which permits identification of transformed calli based on the presence of the marker introduced as part of the exogenous DNA. Conveniently, the selective media is placed in a petri dish with portions of the calli, typically about 100 mg each. The selection medium is a general growth medium, such as N12 or M53 (as described in the Experimental section hereinafter) supplemented with the plant selection agent, and usually including the anti-Agrobacterium antibiotic. Suitable plant selection agents include the following.

| Antibiotic Resistance | Concentration of Antibiotic Selection Medium |
|---|---|
| kanamycin | 200–500 mg/l |
| hygromycin | 20–80 mg/l |
| spectinomycin | 20–80 mg/l |
| streptomycin | 100–500 mg/l |
| chlorsulfuron | 0.001–0.05 mg/l |

Preferred selection media are N12 and M53 (see Experimental section hereinafter) containing no cytokinin or auxins, but having abscisic acid added at from about 0.5 to 4 mg/l, preferably at about 2 mg/l. M53 (see Experimental section hereinafter) is particularly preferred when the callus structures are sized from about 0.4 to 0.7 mm. When kanamycin resistance is the selectable marker, N12CK and M53CK (see Experimental section hereinafter) are particularly suitable.

The selection culture will be maintained for a time sufficient to permit transformed callus cells to grow and produce white-cream colored calli, while the non-transformed callus cells turn brown and die. Typically, the selection culture will last from about 25 to 50 days, depending primarily on the concentration of the plant selective agent. For example, thirty days is generally sufficient for kanamycin at 300 mg/l, while fifty days is suitable for kanamycin at 200 mg/l. The primary criterion in ending the selection culture, however, is a clear distinction between proliferating cells which have been transformed and non-proliferating cells which have not been transformed.

While viability is indicative that the callus cells have been transformed, it is usually desirable to confirm transformation using a standard assay procedure, such as Southern blotting, Northern blotting, restriction enzyme digestion, polymerase chain reaction (PCR) assays, or through the use of reporter genes. Suitable reporter genes and assays include β-glucuronidase (GUS) assays as described by Jefferson, *GUS Gene Fusion Systems User's Manual*, Cambridge, England (1987) and luciferase assays as described by Ow (1986) *Science* 234:856–859. It will be appreciated that these assays can be performed immediately following the transformation procedures or at any subsequent point during the regeneration of the transformed plant materials according to the present invention.

Following transformation, the calli are transferred to a maintenance medium for generation of somatic embryos. This medium contains as its principle elements an auxin, a cytokinin, an energy source, and an appropriate nutrient medium such as White's or B5 media. The maintenance medium will also include an anti-Agrobacterium antibiotic and, usually, ABA or gibberellic acid.

The formulation of the maintenance medium may be adjusted depending on the source of somatic tissue. If the mature somatic tissue was obtained from a stamen filament or cell suspension culture, the ratio of auxin to cytokinin may be decreased by a factor of at least two and up to as much as 15 relative to the ratio of auxin to cytokinin present in callus induction medium and/or the source of the auxin and cytokinin in the regeneration will differ from the source of the auxin and cytokinin in the callus induction medium. In a preferred embodiment, a weaker cytokinin and auxin is used in the regeneration media than in the induction media and selection medium. Specifically, 2,4-D is a stronger auxin, i.e., has a greater effect on growth regulation than NAA and zeatin is a stronger cytokinin than kinetin. As an example, regeneration of filaments can occur in a medium comprising 2,4-D/zeatin at a ratio of 1.3, compared with NAA/kinetin at a ratio of 4.0 in callus induction medium.

If the mature somatic tissue was obtained from a leaf explant, the ratio of auxin to cytokinin may be increased relative to the ratio of auxin to cytokinin present in callus induction medium and/or the source of the auxin and cytokinin in the regeneration medium will differ from the source of the auxin and cytokinin in the callus induction medium. As an example, regeneration of leaf explants can occur in a maintenance medium comprising NAA/KIN at a ratio of 2.0 compared with 2,4-D/zeatin at a ratio of 1.3.

Preferred maintenance media are M53C (particularly if N12CK was the selection medium) and M20C (particularly if M53CK was the selection medium).

The period on maintenance medium for regeneration generally takes about 20 to 60 days, usually about 30 days. Globular to heart-shaped embryos will usually be apparent on the surface of the culture after this time. In many cases, the embryos so formed are capable, upon subculture, to give rise on their outer surface to secondary embryos. If this secondary embryo production is specifically desired, the globular embryos can be transferred to fresh regeneration media and cultured from 3 to 6 weeks.

The somatic embryos produced on the maintenance medium as just described can be repeatedly subcultured in order to provide for an increased number of transformed embryos. In order to reproduce whole plant material, however, it is desirable that the somatic embryos be subjected to a maturation process.

Maturation of somatic embryos is accomplished by transfer of globular embryos to a medium comprising nutrients, an energy source, and a growth regulator which may include but is not limited to an auxin, a cytokinin, abscisic acid, and gibberellic acid. The auxins may be any auxin, natural or synthetic, for example, IAA, NAA, 2,4-D, and picloram. The auxin will be present in an amount of about 0.1 to 10 mg/ml. The cytokinin may be selected from any of the known cytokinins, natural or synthetic, for example, 6-BA, ZEA, KIN, and iP. A cytokinin may be present in an amount of about 0.2 to 15.0 mg/ml. Abscisic acid may be present in the amount of about 0.2 to 2 mg/l. Gibberellic acid may be present in the amount of about 0.5 to 5 mg/l. A preferred maturation medium is M20 (see Experimental section hereinafter).

Callus cells are held on the maturation medium with subculturing preferably about every 30 days, until mature somatic embryos are obtained. The period of maturation generally takes about three to six weeks. Globular embryos will appear on the surface of the maturation medium, with many embryos giving rise on their outer surface to secondary embryos. If such secondary embryo production is desired, the globular embryos can be transferred to fresh maintenance medium (as described above) and can be subcultured repeatedly in order to provide a greater number of embryos. Such subculturing is preferably performed on M20 medium.

The mature somatic embryos produced as described above are next transferred to a germination medium in order to produce germinated embryos. The germination medium comprises nutrients and an energy source. The medium may further comprise a growth regulator which may include but is not limited to a cytokinin, abscisic acid, and gibberellic acid. The cytokinin may be present at a concentration of about 0.1 to 1.0 mg/l. Abscisic acid may be present in the amount of about 0.2 to 2 mg/l. Gibberellic acid may be present in the amount of about 0.5 to 5 mg/l. The germination media may also further comprise coconut water at about 5 to 15%, v/v. A preferred germination medium is M13. The somatic embryos are held on the germination medium for from about 1 to 45 days, usually about 24 days, to yield germinated embryos.

Early stages of embryo germination are characterized by hypocotyl elongation, cotyledonary leaves and chlorophyll development. In late stages of germination, cotyledonary leaves enlarge, the hypocotyl elongates, and a tap root develops. The differentiated embryos may be cultured on germination media for about 1 to 4 weeks. The result is somatic embryos with shoots 1 to 4 mm in length having from 2 to 4 leaves.

Optionally, the germinated embryos may be transferred to a shoot elongation medium to produce elongated shoots. The medium will include nutrients, an energy source, and growth regulators, generally as described above, but will have a reduced salt concentration (up to 50% lower) and a reduced growth regulator content, preferably BA at 1 to 6 mg/l and IAA at 0.1 to 1 mg/l. A preferred shoot elongation medium is M13-8 (see Experimental section hereinafter). The embryos are maintained in the elongation medium until the shoots are about 10 to 20 mm in length and develop three to five fully green and elongated leaves and stems, typically requiring three to four weeks.

The germinated (and optionally shoot elongated) embryos are subsequently transferred to a propagation (or shoot multiplication) medium which comprises appropriate nutrients, an energy source, an auxin, and a cytokinin. The auxin may be any auxin, natural or synthetic, for example, IAA, NAA, 2,4-D and picloram. The auxin will be present in an amount of about 0.1 to 10 mg/l. The cytokinin may be selected from any of the known cytokinins, natural or synthetic, for example, 6-BA, ZEA, KIN, and iP. A cytokinin may be present in an amount of about 0.2 to 15.0 mg/l. In a preferred embodiment, the auxin is IAA, present at a concentration of about 0.3 mg/l and the cytokinin is 6-BA, present at a concentration of about 3.0 mg/l. A preferred propagation or shoot multiplication medium is M13 (see Experimental section hereinafter).

The germinated embryo may be cultured in propagation medium for about 20 to 200 days, preferably about 30 days. Well developed plantlets may be obtained and can be transferred to, for example, artificial soil for root regeneration. In one embodiment, multiple shoots can be isolated from one single plantlet before transferring to soil.

Well developed shoots, typically having a length in the range from about 10 to 40 mm and preferably having from about 5 to 10 leaves, are selected for root regeneration. The preferred method for root regeneration is to transfer the shoots to be rooted into small pots containing an artificial soil, typically saturated with a medium containing root inducing hormones. A suitable root induction contains nutrients but is deprived of sugar and other energy sources. The medium may further contain thiamine, preferably in the form of thiamine-HCl at about 0.5 to 2 mg/l, and an auxin, such as IAA at about 1 to 4 mg/l. A preferred root regeneration medium is N3-4 (see Experimental section hereinafter). While in the pots, the shoots may be placed in a container, such as a magenta GA-7 culture container and incubated in a growth chamber preferably under a regime of 16 hours light per 24 hour period.

An alternate regeneration method is to dip the shoots in a suitable root-inducing hormone, such as RooTone™. The shoots are then placed directly in the soil in the greenhouse, preferably being maintained under a plastic cover to maintain a high relative humidity. The cover can be gradually removed over a period of days in order to cause hardening of the shoots.

With either of the above approaches, roots are typically obtained in about 7 to 35 days. The rooted shoots can then be transplanted within the greenhouse or elsewhere in a conventional manner for tissue culture plantlets.

Transformation of the resulting plantlets can be confirmed by assaying the plant material for any of the phenotypes which have been introduced by the exogenous DNA. In particular, suitable assays exist for determining the presence of certain reporter genes, such as β-glucuronidase and/or luciferase, as described hereinabove. Other procedures, such as PCR, restriction enzyme digestion, Southern blot hybridization, and Northern blot hybridization may also be used.

The following examples are offered by way of illustration, not by way of limitation.

| EXPERIMENTAL MATERIALS | |
|---|---|
| Abbreviations/Names | Source/Reference |
| ABA; Abscisic Acid | Sigma Chemical Co., St Louis, MO, USA |
| Acetosyringone | Aldrich Chemical Co., Milwaukee, WI, USA |
| Agar; TC Agar | Hazleton Biologics, Inc., Lenexa, KS, USA |
| As; Acetosyringone | Aldrich Chemical Co., Milwaukee, WI, USA |
| B-5 Salts | Gamborg et al. (1968) Exp. Cell Res. 50:151–158 |
| BA; Benzyl Adenine | Sigma Chemical co., St. Louis, MO, USA |
| Bactogar | Difco, Detroit, MI, USA |
| Carbenicillin | Geopen |
| 2,4-D; 2,4-Dichlorophenoxyacetic Acid | Sigma Chemical Co., St. Louis, MO, USA |
| Dropp, a cotton defoliant whose active ingredient is thidauzuron | Nor-Am Chemical Co., Wilmington, DE, USA |
| $GA_3$; Gibberellic Acid | Sigma Chemical Co., St. Louis, MO, USA |
| G418; Geneticin | Sigma Chemical Co., St. Louis, MO, USA |
| Gel-rite ® | Scott Lab. Inc., Warwick, RI, USA |
| GUS; β-glucuronidase | |
| IAA; Indole-3-Acetic Acid | Sigma Chemical Co., St. Louis, MO, USA |
| IBA; Indole Butyric Acid | Sigma Chemical Co., St. Louis, MO, USA |
| Insolitol | Sigma Chemical Co., St. Louis, MO, USA |
| Jiffy Mix | Ball Jiffy, Chicago, IL, USA |
| Jiffy Pots | Ball Jiffy, Chicago, IL, USA |
| Kanamycin, Kanamycin Sulfate | Sigma Chemical Co., St. Louis, MO, USA |
| KIN, Kinetin | Sigma Chemical Co., St. Louis, MO, USA |
| LUC, Luciferase | Analytical Luminescence Lab, San Diego, CA, USA |
| Luciferin, D-Luciferin- | Analytical Luminescence Lab, |

EXPERIMENTAL MATERIALS

| Abbreviations/Names | Source/Reference |
|---|---|
| sodium | San Diego, CA, USA |
| MES, 2-N Morpholino-ethanesulfonic Acid | Sigma Chemical Co., St. Louis, MO, USA |
| MS Salts | JRH Bioscience, Lenexa, KS, USA |
| MS Vitamins | Murashige, et al., Physiol. Plant (1962) 15:473–497 |
| $N_6$ Salts | Chu, et al., Scientia Sinica (1975) 18:659–668 |
| NAA, Naphthalene Acetic Acid | Sigma Chemical Co., St. Louis, MO, USA |
| Nicotinic Acid | Sigma Chemical Co., St. Louis, MO, USA |
| NPT, Neomycinphospho-transferase | |
| Pyridoxine | Sigma Chemical Co., St. Louis, MO, USA |
| RooTone ™ | Cooke Lab Products, Portland, OR, USA |
| TDZ, Thidiazuron | Purified from Dropp by dissolving in dimethylsulfoxide and passing through a 0.2 μm nylon filter. |
| Tetracycline | Sigma Chemical Co., St. Louis, MO, USA |
| Thiamine-HCl | Sigma Chemical Co., St. Louis, MO, USA |
| Triton, TritonX-100 | Sigma Chemical Co., St. Louis, MO, USA |
| Tryptone | Difco-Lab, Detroit, MI, USA |
| Tween ® | ICI United States, Inc., Wilmington, DE, USA |
| Vancomycin | Sigma Chemical Co., St. Louis, MO, USA |
| Vitamins | Sigma Chemical Co., St. Louis, MO, USA |
| X-GUS, 5-Bromo-4-chloro-3-Indolyl-β-D-Glucuronide | Diagnostic Chem. Ltd., Monroe, CT, USA |
| Yeast Extract | Difco-Lab, Detroit, MI, USA |
| Zeatin | Sigma Chemical Co., St. Louis, MO, USA |

MEDIA COMPOSITIONS

M13

| | | |
|---|---|---|
| MS Salts | 1x | |
| Thiamine HCl | 0.5 | mg/l |
| Inositol | 100.0 | mg/l |
| Pyridoxine | 0.5 | mg/l |
| Nicotine Acid | 0.5 | mg/l |
| Glycine | 2.0 | mg/l |
| BA | 3.0 | mg/l |
| IAA | 0.3 | mg/l |
| Aqar | 6.0 | g/l |
| Sucrose | 30 | g/l |
| pH | 5.8 | |

M13-8

Same except:
| | | |
|---|---|---|
| MS Salts | 3/4x | |
| Pyridoxine | 1.5 | mg/l |
| Nicotinic Acid | 1.5 | mg/l |

M20 (alternatively M134-20)

| | | |
|---|---|---|
| MS Salts | 1x | |
| Thiamine HCl | 5 | mg/l |
| Inositol | 100.0 | mg/l |
| Pyridoxine | 1.5 | mg/l |
| Nicotinic Acid | 1.5 | mg/l |
| Glycine | 2.0 | mg/l |
| $GA_3$ | 1.0 | mg/l |
| ABA | 0.2 | mg/l |
| KAO Vitamins* | 1x | |
| Coconut Water** | 10% | v/v |
| Sucrose | 20 | g/l |
| Gel-rite ® | 2.4 | g/l |
| pH | 5.5 | |

*Kao et al., 1975, Planta 126:105
**Not essential

M20C

| | | |
|---|---|---|
| M20 plus carbenicillin | 500 | mg/l |

M20K200C

| | | |
|---|---|---|
| M20C plus kanamycin | 200 | mg/l |

M53

| | | |
|---|---|---|
| MS Salts | 1x | |
| Thiamine HCl | 5 | mg/l |
| Inositol | 20.1 | g/l |
| Pyridoxine | 1.5 | mg/l |
| Nicotinic Acid | 1.5 | mg/l |
| Glycine | 2.0 | mg/l |
| $GA_3$ | 1.0 | mg/l |
| ABA | 2.0 | mg/l |
| Sucrose | 30 | g/l |
| Gel-rite ® | 2.4 | g/l1 |
| pH | 5.5 | |

M53AS

| | | |
|---|---|---|
| M53 plus As | 100 | μM |

M53C

| | | |
|---|---|---|
| M53 plus carbenicillin | 500 | mg/l |

M53CK

| | | |
|---|---|---|
| M53C plus kanamycin | 300 | mg/l |

M130-3

| | | |
|---|---|---|
| MS salts | 1x | |
| MS vitamins | 1x | |
| Glycine | 2 | mg/l |
| KIN | 0.5 | mg/l |
| NAA | 2 | mg/l |
| Sucrose | 30 | g/l |
| Gel-rite ® | 2.4 | g/l |
| pH | 5.7 | |

M134-1

| | | |
|---|---|---|
| MS Salts | 1x | |
| Thiamine-HCl | 5 | mg/l |
| Inositol | 100 | mg/l |
| Pyridoxine | 1.5 | mg/l |
| Nicotinic Acid | 1.5 | mg/l |
| Glycine | 2 | mg/l |
| Zeatin | 1.5 | mg/l |
| NAA | 0.025 | mg/l |
| $GA_3$ | 1 | mg/l |
| Sucrose | 20 | g/l |
| Gel-rite ® | 2.4 | g/l |
| pH | 5.7 | |

M139

| | | |
|---|---|---|
| B-5 salts | 1x | |
| Ammonia Sulfate | 329 | mg/l |
| Thiamine-HCl | 5 | g/l |
| Inositol | 100 | mg/l |
| Pyridoxine | 1.5 | mg/l |
| Nicotinic Acid | 1.5 | mg/l |
| Glycine | 2 | mg/l |
| 2,4-D | 1.55 | mg/l |
| Sucrose | 30 | g/l |
| Gel-rite ® | 2.4 | g/l |
| pH | 5.6 | |

M139-2

M139 modified as follows:
| | | |
|---|---|---|
| 2,4-D | 2.0 | mg/l |
| Zeatin | 1.5 | mg/l |

MEDIA COMPOSITIONS

N3-1

| | |
|---|---|
| N$_6$ salts | 1/2x |
| Thiamine HCl | 1.0 mg/l |
| Sucrose | 20 g/l |
| Gel-rite ® | 2.2 g/l |
| pH | 5.6 |

N3-4

N3-1 modified as follows:

| | |
|---|---|
| NAA without sucrose and Gel-rite ® | 2.0 mg/l |

N12

| | |
|---|---|
| N$_6$ salts | 1x |
| Thiamine HCl | 5 mg/l |
| Inositol | 100.0 mg/l |
| Pyridoxine | 1.5 mg/l |
| Nicotinic Acid | 1.5 mg/l |
| Glycine | 2.0 mg/l |
| 2,4-D: | 5.0 mg/l |
| Zeatin | 1.0 mg/l |
| GA$_3$ | 1.0 g/l |
| KAO Vitamins | 1x |
| Sucrose | 20 g/l |
| Gel-rite ® | 2.4 g/l |
| pH | 5.5 |

N12AS

| | |
|---|---|
| N12 plus As | 100 µM |

N12C

| | |
|---|---|
| N12 plus cabenicillin | 500 mg/l |

N12CK

| | |
|---|---|
| N12C plus kanamycin | 300 mg/l |

MinA

| | |
|---|---|
| KH$_2$PO$_4$ | 10.5 g/l |
| (NH$_4$)$_2$SO$_4$ | 1.0 g/l |
| Sodium citrate.2H$_2$O | 0.5 g/l |
| Agar | 15 g/l |

L-Broth*

| | |
|---|---|
| Tryptone | 10 g/l |
| Yeast Extract | 5 g/l |
| NaCl | 5 g/l |
| Glucose | 1 g/l |
| Agar | 15 g/l |

*pH adjusted to 7.0 to 7.2 using 0.1–5N NaOH, before adding agar; dispense at 25 ml/plate.

METHODS AND RESULTS

Example 1

*Agrobacterium rhizogenes* Transformation of Rose

1. Culture tissue on callus induction medium to yield calli.

Stamen filaments of *Rosa hybrida* L. var. Royalty (obtained from DeVore Nurseries, Watsonville, Calif.) were excised from flower buds of ca. 1.5 cm long, after a cold pretreatment at 2° C. during 14 days. Buds were disinfected with clorox (10%)/Tween-®20 (0.1%) for 20 mins., rinsed three times with sterile deionized water and placed in callus induction medium (M130-3). All media were autoclaved for 20 min. at 24° C. and 15 psi after pH adjustment. Cultures in petri dishes were sealed with Parafilm and kept in the dark at 24° C. A fast-growing, semi-hard, yellow callus was obtained from filament explants after 3 weeks in M130-3. After subculture in this medium, the callus changed to a drier appearance.

The callus was placed in maintenance medium M139. M139 medium improved callus quality preventing oxidation and leading to a less compact callus.

2. Pre-embryogenic callus induction medium and their maintenance.

M139 medium with modified growth regulators 2,4-D (2.0 mg/l) and zeatin (1.5 mg/l), was used as pre-embryogenic friable callus induction medium (M139-2). Early stages of pre-embryogenic calli were observed after 8 weeks of callus culture on M139-2 at a frequency of 1.43%. Globular structures were subcultured on a proliferation medium, M134, KM-8P vitamins (Kao and Michayluk (1975) Planta, 126:105–110) and growth regulators were filter sterilized and added into the autoclaved portion of proliferation medium. After 3 weeks, a very fast-growing friable, and white embryonic tissue with the presence of globular structures was produced. Periodic subculture of this tissue on medium maintained its capacity to proliferate and to produce globular structures. Such tissue was able to be maintained on N12 medium for 8 months.

3. *Agrobacterium rhizogenes* culture and preparation.

*Agrobacterium rhizogenes* wild-type strain 15834 (Birot et al. (1987) Plant Physiol. Biochem. 25:323–325) containing the binary vector pJJ3499 was used for transformation. pJJ3499 contains the nopaline synthase promoter and neomycin phosphotransferase II (NPT II) gene which confers kanamycin resistance as well as the cauliflower mosaic virus 35S promoter. The β-glucuronidase gene (Jefferson (1986) Proc. Natl. Acad. Sci. USA 83:8447–8451) is present as a reporter gene. Strain 15834 alone was used as a control inoculum. Bacteria were maintained on L-broth medium solidified with 1.5% Bactoagar containing 10 mg/l tetracycline. Bacteria were scraped off the solid medium using a loop and suspended in"Induction Broth" medium (Winans et al. (1989) J. Bact. 171:1616–1622) containing 100 µM acetosyringone, and cultured on a shaker (120 rpm) at 28° C. for 3 hours.

4. Cocultivation on cocultivation medium.

Agrobacterium cells were mixed at the volume ratio of 3:1 (plant cell:Agrobacterium cell) with the friable calli selected after 6 months. Calli and Agrobacterium were placed on 7.0 cm sterile Whatman #1 filter paper circles on the top of cocultivation medium N12 supplemented with 100 µM acetosyringone. Plates were placed in a 24° C. controlled environment incubator in the dark for 48 hours.

5. Wash.

Calli were washed from Agrobacterium with the liquid medium N12 supplemented with 500 mg/l carbenicillin. Calli were mixed well with the medium at a volume ratio of 1:10 (calli:medium), centrifuged (500 rpm for 5 min.), and the supernatant was discarded. Washing was repeated 4 times.

6. Selection medium.

After washing, 10–12 chunks (about 100 mg each) of calli were placed and spread on selection medium N12CK containing 300 mg/l kanamycin sulfate for selection and 500 mg/l carbenicillin to kill off the residual Agrobacterium. Tissues remained on this medium for 30 days. At the end of the 30 day culture period, most parts of the calli turned brown, however one to a few sections of each callus started growing to produce white-cream colored calli. 75 out of 81 inoculated calli produced kanamycin-resistant calli (Table 1).

TABLE 1

Recovery of Kanamycin-Resistant Calli on N12 Medium

| Treatment | Kanamycin Level (mg/l) | Number of Chunks Plated on Selection Medium After Cocultivation | Number of Calli Growing 1 month later |
|---|---|---|---|
| Inoculated with 15834 (Example 1) | 300 | 81 | 75 |
| | 0 | 23 | 23 |
| Inoculated with LBA 4404 (Example 2) | 300 | 33 | 25 |
| | 0 | 12 | 12 |
| Uninoculated Control | 300 | 25 | 0 |
| | 0 | 15 | 15 |

7. Culture on maintenance medium to yield somatic embryos.

White-cream colored callus tissues were then transferred to N12C medium containing 500 mg/l carbenicillin (but no kanamycin) or M53C for 23 days. The tissue on N12C was then transferred to medium M53 for three weeks. Calli proliferated further on these media and produced larger globular structures.

8. Culture on maturation medium to yield somatic embryos.

The callus tissue from part 7 was subsequently cultured in maturation medium M20 for either 8 or 11 weeks. On this medium, mature embryos were obtained starting after four weeks and continuing afterwards. Mature embryos appeared on structures with wide cotyledons (usually 2 and occasional 3 or 4) and very short hypocotyl and radical. The embryos were white. The same results were obtained for both the 8 week and 11 week culture period.

9. Culture on germination medium.

Germination of the matured embryonic tissue was accomplished on M13 medium after 2 weeks. Under 16 hr/day light illumination (around 1500 lux) tissues became green, cotyledons expanded 5–10 times, and embryos enlarged in size 3–5 times and produced 1–5 green shoots.

10. Culture on shoot multiplication medium.

Germination embryos were subcultured on fresh M13 medium. On this medium shoots multiplied further, and after 4 weeks, ten to 30 shoots per original embryo were produced.

11. Culture on shoot elongation medium.

Sections of the shoot clusters were cut off and transferred to M13-8 medium with 4–6 shoots per cluster. Shoots elongated to 10–15 cm in size within 3–4 weeks.

12. Culture on artificial soil for root regeneration.

Shoots were cultivated in Jiffy Mix saturated with N3-4 medium. After 6 weeks, well developed shoots were obtained and were in condition for transfer to artificial soil.

13. Culturing shoots in soil for root regeneration.

Shoots were dipped in RooTone™ and planted in a mix soil (3:1 Super Soil: Perlett, Rod Mclellan Co., So. San Francisco, Calif. USA) in greenhouse and watered as needed. After 3 weeks roots were regenerated and complete transgenic plants were obtained. Plants were covered with a plastic sheet which was gradually (within 2 weeks) removed to harden off the plants.

14. Results and demonstration of transformation.

Transformation was confirmed by several means: 1) transformed calli transferred onto M20K200C were able to continue their growth, whereas nontransformed control calli stopped growth on the medium, turned brown and eventually died (Table 2); 2) transformed calli, somatic embryos, and leaf sections from transformed shoots all tested positive and nontransformed controls tested negative in the GUS assays (Table 3) (transformants stained blue and nontransformed tissues did not stain blue).

Leaf callus assays were performed on five transgenic shoots. The medium contained 50 mg/l kanamycin to verify that the tissues had been transformed. All transformants formed calli in the presence of the kanamycin, thus confirming transformation.

TABLE 2

Assay for Kanamycin Resistance of Embryogenic Calli on M20 Medium

| Embryonic Calli | # Calli | Kanamycin Level (mg/l) | # Resistant Surviving Calli |
|---|---|---|---|
| Putative 15834- Transformed Calli (Example 1) | 43 | 200 | 43 |
| | 40 | 0 | 40 |
| Putative LBA4404- Transformed Calli (Example 2) | 23 | 200 | 23 |
| | 10 | 0 | 10 |
| Untransformed Controls | 25 | 200 | 0 |
| | 25 | 0 | 25 |

TABLE 3

| | GUS Assays[1] | | |
|---|---|---|---|
| Tissue Materials | No. Tested | No. Positive | Percent Positive |
| Friable cells | 65 | 65 | 100 |
| Embryonic Calli | 38 | 38 | 100 |
| Somatic Embryos | 41 | 40 | 98 |
| Shoots | 16 | 16 | 100 |
| Plants | 2 | 2 | 100 |

[1] Assays performed as described in Jefferson (1987), supra.

Example 2

*Aarobacterium tumefaciens* Transformation of Rose

Figure 2:
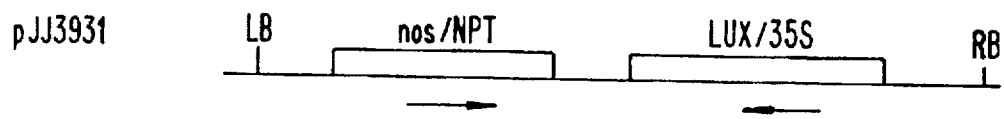
FIG. 2 illustrates the T-DNA region of plasmid pJJ3491 used in Example 2 of the Experimental section hereinafter. Plasmid pJJ3931 carries a nos/NPT fusion and a 35S/luciferase fusion.

1. Culture tissues on callus induction medium to yield calli.
   Same as Example 1.
2. Pre-embryogenic callus induction medium and their maintenance.
   Same as Example 1.
3. *Agrobacterium tumefaciens* culture and preparation.
   Same as Example 1 except *Agrobacterium tumefaciens* strain LBA4404 (Hoekema et al. (1983), supra.) containing the binary vector pJJ3931 (FIG. 2) was used for transformation. pJJ3931 is same as pJJ3499 except that it carries the luciferase (-LUC) gene (Ow et al. (1986), supra.) instead of GUS, under the control of 35S promoter, used as a reporter gene.
4. Cocultivation on cocultivation medium.
   Same as Example 1.
5. Wash.
   Same as Example 1.
6. Selection medium.
   Same as Example 1 except that 25 out of 33 inoculated calli produced kanamycin-resistant calli (Table 1).
7. Culture on maintenance medium to yield somatic Embryos.

Same as Example 1.
8. Culture on maturation medium to yield mature somatic Embryos.
Same as Example 1.
9. Culture on germination medium.
Same as Example 1.
10. Culture on shoot multiplication medium.
Same as Example 1.
11. Culture on shoot elongation medium.
Same as Example 1.
12. Culture on artificial soil for root regeneration.
Same as Example 1, except shoots were cultured in Jiffy Pots saturated with N3-4 medium. After four weeks, complete plants were transferred to soil.
13. Transfer to soil.

Complete plants were transferred to soil and incubated in a growth chamber (16 hr/day light, 16° C. night, 24° C. day temperature) for 2 weeks. Plants were covered with plastic which was gradually removed over 2 weeks to harden off the plants.

14. Results and demonstration of transformation.

Figure 3:
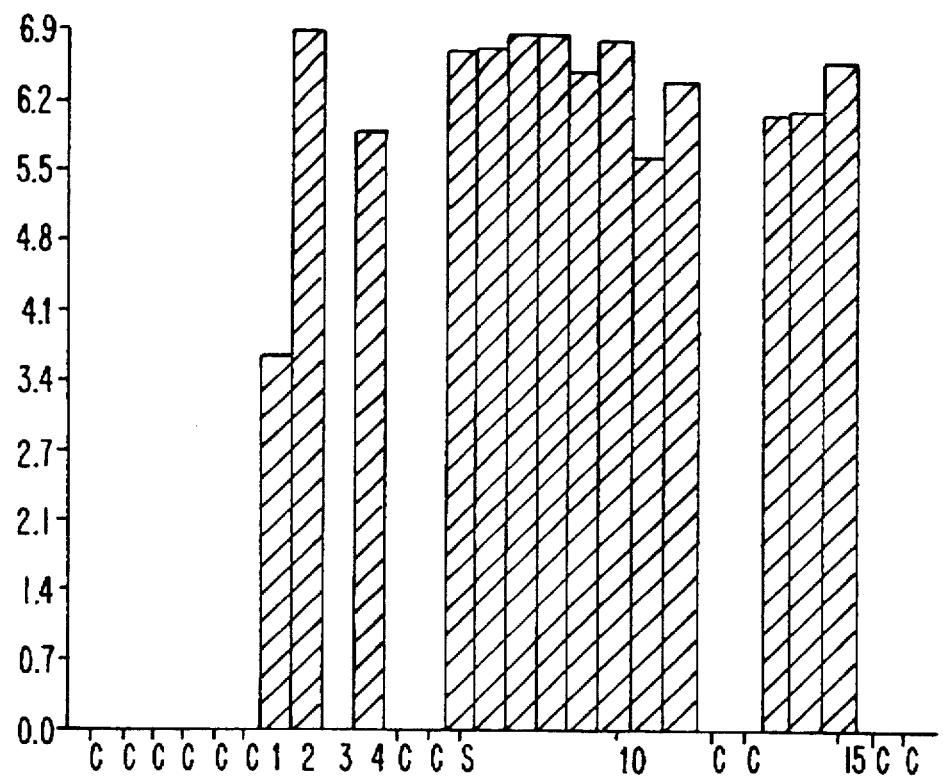
FIG. 3 is a bar graph of luminescence measurements from transformed rose embryogenic calli bearing the firefly luciferase gene. Fifteen putative transformed calli (no. 1–15) and 12 non-transformed control calli (designated by C) were placed individually in 60 μl of 200 μM luciferin solution in 1.5 ml microcentrifuge tubes for 30 minutes in the dark. The tubes then were placed in scintillation vials and measured in a scintillation counter (Packard Instrument Co., Downers, Grove, Ill., USA). The bars represent the number of light units emitted from each sample in terms of log scale of cpm (counter per minute). The assay was performed generally as described in Ow et al. (1986) Science 234:856–859.

Transformation was confirmed by several means: 1) transformed calli were able to continue growth on M20 K200C medium (Table 2) and 2) most transformed calli tested positive and non-transformed calli tested negative in a LUC assay (Table 4 and FIG. 3)

TABLE 4

| Tissue Materials | LUC Assay[1] | | |
|---|---|---|---|
| | # Tested | # Positive | % Positive |
| Friable Calli | 15 | 14 | 93 |
| Embryogenic Calli | 13 | 13 | 100 |

[1]Assays performed as described in Ow (1986), supra.

Although the foregoing invention has been described in detail for purposes of clarity of understanding, it will be obvious that certain modifications may be practiced within the scope of the appended claims.

What is claimed is:

1. A method for genetically transforming callus cells from a rose plant, said method comprising:
   incubating friable, granular callus cells with Agrobacterium cells carrying an exogenous DNA sequence; and
   selecting callus cells which express at least a portion of the exogenous DNA sequence.

2. A method as in claim 1, wherein the callus cells and the Agrobacterium cells are incubated in a medium containing nutrients, an energy source, and a virulence induction compound for a time period from about one day to about four days.

3. A method as in claim 1, wherein pre-embryogenic callus cells are incubated with the Agrobacterium cells.

4. A method as in claim 1, wherein the exogenous DNA sequence includes a selectable marker gene and the callus cells are selected in a selection medium which inhibits the growth of cells which do not express the selectable marker gene.

5. A method for genetically transforming a rose plant, said method comprising:
   (a) culturing tissue from the rose plant under conditions selected to produce a friable, granular callus;
   (b) incubating cells from the callus of step (a) with Agrobacterium cells carrying an exogenous DNA sequence;
   (c) selecting callus cells from step (b) which express at least a portion of the DNA sequence; and
   (d) producing transformed plantlets from the selected callus cells of step (c).

6. A method as in claim 5, wherein the tissue is derived from a plant part selected from the group consisting of stamen filaments, leaf explants, stem sections, shoot tips, petal, sepal, petiole, and peduncle.

7. A method as in claim 6, wherein the tissue is cultured until a hardened callus is produced, further comprising cutting the callus into sections prior to incubating.

8. A method as in claim 5, wherein pre-embryogenic callus cells are incubated with the Agrobacterium cells.

9. A method as in claim 5, wherein the exogenous DNA sequence includes a selectable marker gene and the callus cells are selected in a selection medium which inhibits the growth of cells which do not express the selectable marker gene.

10. A method as in claim 5, wherein the transformed plantlets are produced by:
    culturing the selected callus cells in a maintenance medium selected to produce somatic embryos;
    culturing the somatic embryos in a maturation medium selected to produce differentiated somatic embryos;
    culturing the differentiated somatic embryos in a germination medium selected to induce shoot and leaf formation on the embryos; and
    rooting the germinated embryos to produce the plantlets.

11. A rose callus cell derived from an explant material which has been transformed with an exogenous DNA sequence according to the method claim 1, said DNA sequence comprising a functional gene capable of imparting a phenotype not possessed by the explant material, wherein said DNA sequence has been integrated into the rose chromosomes.

12. A rose plant having cells derived from an explant material which have been transformed with an exogenous DNA sequence according to the method claim 5, said DNA sequence comprising a functional gene capable of imparting a phenotype not possessed by the explant material, wherein said DNA sequence has been integrated into the rose chromosomes.

13. A rose callus cell produced by the method in claim 1.

14. A rose plant produced by the method of claim 5.

15. A somatic rose embryo produced by the method comprising:
    (a) culturing tissue from a rose plant on a callus induction medium containing nutrients, an energy source, an auxin, and a cytokinin in amounts effective to induce callus formation;
    (b) combining cells from the callus of step (a) with Aqrobacterium cells carrying the exogenous DNA sequence in a cocultivation medium containing nutrients, an energy source, and an induction compound under conditions which allow the Agrobacterium cells to infect the callus cells and transfer the exogenous DNA sequence to the callus cell chromosomes;
    (c) culturing callus cells from step (b) in a selection medium containing nutrients, an energy source, an auxin, a cytokinin, and an agent which inhibits the growth of callus cells which do not express the selectable marker gene; and
    (d) culturing the cells selected in step (c) in a maintenance medium containing nutrients, an energy source, an antibacterial agent, and a growth regulator, other than an auxin or a cytokinin, present in amounts effective to produce somatic embryos.

* * * * *